United States Patent [19]

Gimbel

[11] Patent Number: 4,864,661
[45] Date of Patent: Sep. 12, 1989

[54] PUNCTURE RESISTANT SURGICAL GLOVE

[76] Inventor: Neal I. Gimbel, 5815 N. 21st Dr., Phoenix, Ariz. 85016

[21] Appl. No.: 260,463

[22] Filed: Oct. 20, 1988

[51] Int. Cl.⁴ .............................................. A41D 19/00
[52] U.S. Cl. ....................................... 2/167; 2/161 R; 2/168
[58] Field of Search .............. 2/167, 168, 159, 161 R, 2/21, 163

[56] References Cited

U.S. PATENT DOCUMENTS

| | | | |
|---|---|---|---|
| 1,250,150 | 12/1917 | du Bois | 2/167 X |
| 3,184,756 | 5/1965 | De Luca, Jr. | 2/21 X |
| 3,511,242 | 5/1970 | Agnone | 2/21 X |
| 4,526,828 | 7/1985 | Fogt et al. | 2/167 X |
| 4,578,826 | 4/1986 | Adiletta | 2/167 |
| 4,742,578 | 5/1988 | Seid | 2/168 X |
| 4,779,290 | 10/1988 | Welch et al. | 2/161 R |

FOREIGN PATENT DOCUMENTS 1097408  5/1986  Japan ..................................... 2/168

Primary Examiner—Werner H. Schroeder
Assistant Examiner—Sara M. Current
Attorney, Agent, or Firm—Tod R. Nissle

[57] ABSTRACT

An improved surgical glove. The glove is puncture resistant at selected areas on the glove. The remaining areas of the glove which attached to the puncture resistant areas are elastic and conform to the hand to maintain the puncture resistant areas in position against the hand.

7 Claims, 1 Drawing Sheet

PUNCTURE RESISTANT SURGICAL GLOVE

This invention relates to gloves.

More particularly, the invention relates to a hand conforming elastic surgical glove which is puncture resistant at certain selected areas on the glove and therefore reduces the likelihood that surgeons and other medical personnel will contract AIDS, hepatitis and other deadly diseases while performing surgery, drawing blood, or otherwise administering to the needs of patients.

In another respect, the invention relates to a puncture resistant surgical glove which, while including selected areas of puncture resistant material, elastically conforms to the hand of a surgeon and snugly maintains the puncture resistant material against the surgeon's hand.

In a further respect, the invention relates to a puncture resistant surgical glove which includes a puncture resistant woven material which is pliable and tends not to impede the normal movement of the articulations of the fingers of the hand of a surgeon.

Surgeon's gloves have long been manufactured from latex and similar materials because of the necessity of providing protective gloves which permit the surgeon to freely move his fingers and to utilize the tactile sensations in his fingertips. Such gloves are manufactured by dipping an aluminum mold into a vat containing a latex mixture, by allowing the layer of latex on the mold to dry and if desired, by repeating the dipping and drying process to form multiple layers of latex on the mold. The mold has the general shape of a hand with fingers extended. The dried latex is then vulcanized or otherwise cured. When worn, latex gloves elastically stretch and conform to the hand of a surgeon, and due to the thinness of the latex composition comprising the glove, enable a surgeon to freely manipulate his fingers, and to utilize his sense of touch.

Protective gloves are crucial for a surgeon because of hepatitis, AIDS, and other diseases which a surgeon can contract when the blood or body fluid of a patient contacts an open cut or passes through the skin into the tissue of the surgeon. However, conventional latex surgical gloves are readily punctured by a hypodermic needle or scalpel blade. Since the puncturing of surgical gloves is a common occurrence, surgeons and other medical personnel have long run the risk of contracting hepatitis, a serious and potentially fatal disease. While the susceptibility of surgical gloves to punctures and tears has long been known, surgical gloves have continued to be fabricated from latex and latex-like material because the gloves must be thin, pliable and elastically conform to the hand. Even the advent of AIDS during the last several years has not adversely affected the use of latex surgical gloves.

AIDS is incurable, and causes destruction of the brain and nervous system, producing dementia prior to death. The symptoms of hepatitis which occur prior to death are similarly undesirable. The fatal aspects of these and similar diseases have not provided sufficient impetus to cause the puncture susceptibility of latex surgical gloves to be remedied.

Accordingly, it would be highly desirable to provide improved surgical gloves which would, while permitting a surgeon and other allied health care providers to retain the ability to readily manipulate their fingers, provide increased resistance to being punctured by hypodermic needles, scalpels, or other sharp or pointed medical instruments.

Therefore, it is a principal object of the invention to provide improved surgical gloves.

A further object of the invention is to provide improved surgical gloves which resist puncture at selected areas on the glove and which generally permit a surgeon or other medical attendant to freely move his fingers while wearing the glove and to retain tactile sensation through the gloves.

Another object of the invention is to provide improved surgical gloves which are puncture resistant at selected areas on the glove and which can be manufactured by utilizing the conventional process in which an aluminum mold is dipped in a latex bath.

These and other and further and more specific objects of the invention will be apparent to those skilled in the art from the following detailed description thereof, taken in conjunction with the drawings, in which.

Briefly, in accordance with my invention, I provide an improved surgical glove including a plurality of stalls each for one of the digits of a hand, at least one of said stalls including a puncture resistant section normally positioned over at least a portion of the inner surface of the digit and including a thin elastic section attached to the first section and extending continuously around and elastically conforming to the digit and maintaining the first puncture resistant section against the portion of the inner surface of the digit. The puncture resistant portion includes strands having a weave selected from the class consisting of biaxial weave, triaxial weave, knit, multiaxial multilayer warp knit, three dimensional cylindrical construction, three dimensional braiding, three dimensional orthogonal, and angle interlock construction.

In an alternate embodiment of the invention, I provide and improved glove including a plurality of stalls each for one of the digits of a hand, at least one of the stalls including a puncture resistant section normally positioned over at least a portion of the inner surface of the digit and including a thin elastic section attached to the first section and extending continuously around and elastically conforming to the digit and maintaining the first puncture resistant section against the portion of the inner surface of the digit. The puncture resistant portion includes a thin panel having a generally smooth continuous outer surface.

The puncture resistant portions of the glove include at least one material from the class consisting of polymers, metal based materials (including metal alloys), ceramics, elastomers, composites and their laminates, composite combinations or blends.

These composite could include but would not be limited to polymer-matrix composites, metal matrix composites, elastomers or rubber based composites, and hybrid composites.

Figure 1:
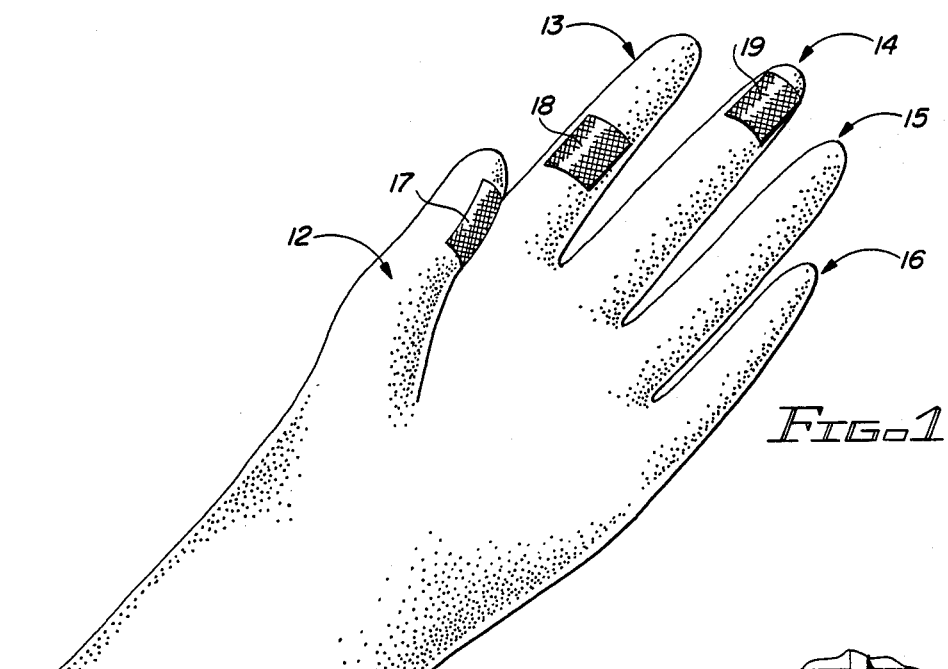
FIG. 1 is a perspective view illustrating a surgical glove constructed in accordance with the principles of the invention.

Turning now to the drawings which depict the presently preferred embodiments of the invention for the purpose of illustrating the practice thereof and not by way of limitation of the scope of the invention and in which like characters represent corresponding elements throughout the several views, FIG. 1 illustrates a surgical glove generally identified by reference character 11 and including elongate stalls 12 to 16 for the thumb and finger digits of a surgeon's hand. In FIG. 1 the portion of the glove which is visible would cover the inner wrist, palm and finger surfaces of the hand. Stalls 12 to 14 include puncture resistant portions 17 to 19, respectively. When glove 11 is worn by a surgeon, portions 17 to 19 are each positioned over a segment of a finger intermediate the joints of a finger so as not to interfere with the bending of the joint of the finger. If, however, a puncture resistant portion 17 to 19 is pliable, it can be positioned over the joint of a finger.

Puncture resistant portion 17 is illustrated in FIG. and comprises a woven fiberglass fabric, called S-2 glass, produced by Owens-Corning Fiberglass Corp. The weave in FIG. is biaxial, however triaxial weave, knit, multiaxial multilayer warp knit, three dimensional cylindrical construction, three dimensional braiding, three dimensional orthogonal, or angle interlock construction can be utilized. These weaves are illustrated on pages 194 and 195 of the October 1986 volume of Scientific American, the entire volume of which is incorporated herein by reference.

Figure 2:
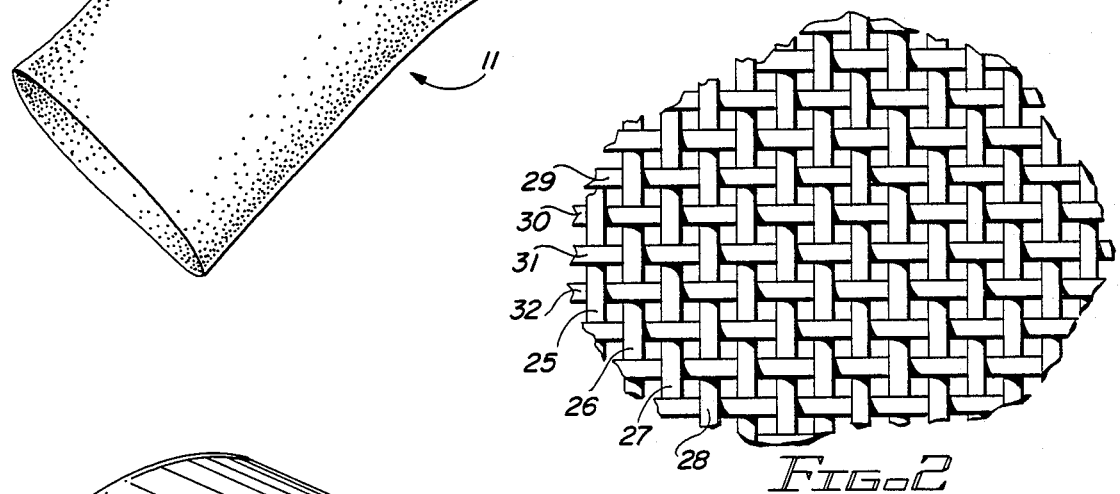
FIG. 2 is a perspective view illustrating a woven puncture resistant portion of the glove of FIG. 1.

In FIG. 2 each strand 25 to 32 of material can comprise the same substance or same composite of substances. Strands of different materials can be combined as desired. For example, strands 25 to 28 can comprise or include Owens-Corning Corning Fiberglass Corporation's S-2 glass while strand 29 to 32 can comprise Dupont's Kelvar organic aramid fiber. Kelvar has a high strength to weight ratio, high impact strength, RF transparency, and good thermal stability and chemical resistance. When a weave of Kelvar is impacted with a needle or other sharp instrument, the Kelvar fibers stretch to disperse impact energy from the stretch fibers to other fibers in the fabric weave. Further energy can be absorbed by Kelvar fabric parallel to the path of the needle or other surgical instrument. Similarly, ballistic nylon, reinforced fiberglass, or Allied Fiber's Spectra 900 high modulus polyethylene fiber can be utilized.

Figure 3:
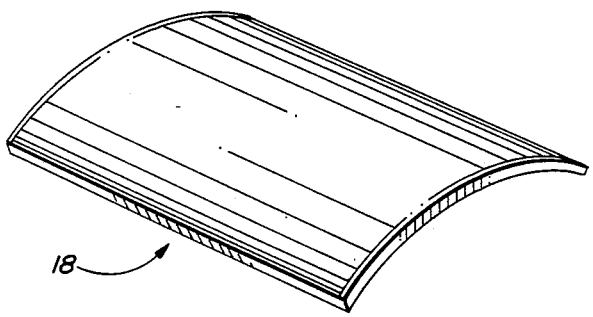
FIG. 3 is a top view illustrating another puncture resistant portion of the glove of FIG. 1.

In FIG. 3, thin panel puncture resistant comprises a solid piece of Dupont's Kelvar aramid. Portion 18 could alternatively comprise a hard ceramic like the boron carbide or sintered silicon carbide ceramics produced by Norton Co. or could comprise another polymer; metal alloy or composite material.

Figure 4:
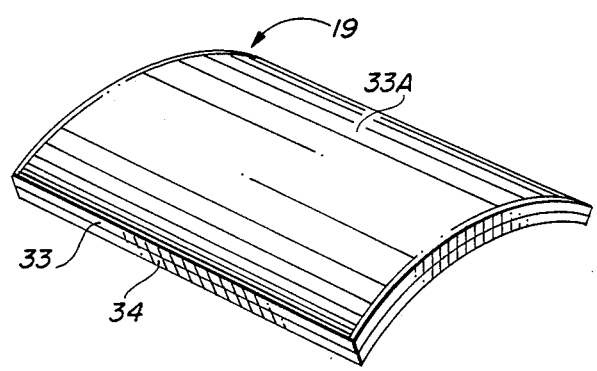
FIG. 4 is a perspective view illustrating another puncture resistant portion of the glove of FIG. 1.

The thin panel puncture resistant panel portion illustrated in FIG. 4 comprises a layer of boron carbide 33 with a Dupont Kelvar backing 34. A thin layer of ballistic nylon spall can be placed on and over smooth continuous top surface 33A of layer 33.

In FIG. 2, each strand in a strand pair 25-26, 26-27, 27-28, 29-30, 30-31, and 31-32 is shown spaced apart. While this arrangement can be utilized, it is preferred that each strand in a strand pair be adjacent and touching the other strand in the pair.

Apart from puncture resistant portions 17 to 19, each finger stall 12 to 16 and the remainder of the glove in FIG. 1 consists of a conventional elastic latex or latex like material. When glove 11 is placed on the hand of surgeon or other medical attendant, the latex material stretches around and conforms to the fingers and hand of the surgeon and maintains puncture resistant portions 17-19 in position over the inner surfaces of the surgeon's fingers. While puncture resistant portions 17 to 19 can be included in glove 11 at any location therein, accidental punctures normally occur on portions of stall 12-14 covering the thumb and first two fingers of a hand.

Puncture resistant portion 18 can comprise a clear puncture resistant polyethylene material of the type included in the "BG" bag recently introduced by Cryovac. Cryovac is a division of W. R. Grace, Company. The BG bag is noted on page 127 of the May 1987 issue of *Packaging Magazine,* incorporated herein by reference. Other puncture resistant plastics and rubbers can be utilized. The Cryovac BG bag is presently utilized in Cryovac 8300 rotary chamber vacuumizers.

In one method of producing gloves in accordance with the invention, a conventional aluminum mold in the shape of a human hand with fingers extended is produced. The palm, finger, etc. surfaces of the aluminum mold are generally smooth and do not reflect the skin wrinkles, fingernails, etc. found on an actual human hand. The mold is dipped in a latex bath and a puncture resistant portion 17 to 19 is pressed, onto the latex on the mold prior to the latex's drying. After the latex dries, the mold is preferably again dipped in the latex bath to coat the puncture resistant portion with a layer of latex. After the second layer dries, the glove can be dipped in the bath as many times as desired. Prior to pressing the puncture resistant portion 17 to 19 onto a wet coat of latex, the aluminum mold can also be dipped in the latex bath to form as many coats as desired. After the latex coatings have dried, the glove is vulcanized or otherwise cured. Other methods of production may also be utilized.

When the material(s) comprising puncture resistant portion 17 to 19 is elastic and relatively thin, it can be utilized to fabricate most or all of glove 11.

As would be appreciated by those of skill in the art, a wide variety of puncture resistant materials can be utilized in fabricating the glove of the invention. By way of example, materials described in the October 1986 volume of Scientific American in articles beginning on pps. 50, 58, 66, 92, 102, 118, 126, 136, 146, 158, 168, 178 and 192, can, if they have greater puncture resistance than conventional latex surgical gloves, be utilized in practicing the invention.

In FIG. 4, layer 33 can, instead of comprising boron carbide or silicon carbide ceramic, comprise a single crystal of aluminum oxide (a transparent ceramic) or can comprise a thin coating of aluminum, steel, silver, or other metal. Strands 25 to 32 can be formed from metals, ceramics, polymers, composites other puncture resistant materials.

Polymer materials, particularly ethylene copolymer materials, are preferred in the practice of the invention. However, such polymer materials must have an unusual assortment of physical properties to function in accordance with the surgical glove of the invention. As is well known, conventional latex surgical gloves have little, if any, puncture resistance. The puncture resistance of the copolymer glove of the invention is indicated by puncture resistance tests under ASTM D-1709 and under a Conventional Puncture Force Test (CPFT) in which a piece of test material clamped in the collar having a five inch diameter open area (e.g. the test material, when clamped in the collar has a five inch diameter area exposed within the inner diameter of the collar) and is contacted at its center (e. g., is contacted at the center of the circular exposed five piece of test material) by a 0.5" inch diameter spherical probe traveling at ten inches per minute. In the puncture resistant surgical glove of the invention, the puncture resistance under ASTM D-1709 (Method ) is in excess of 500 grams for a 1.0 mil film thick piece of material used to manufacture the glove. Under the CPFT, the glove of the invention has a puncture force in excess of 200 ft-lb/in when the glove is made from a 1.0 mil thick piece of material.

The surgical glove of the invention preferably has a puncture resistance under ASTM D-1709 in excess of 700 grams (for a 1.0 mil thick piece of material) and has a puncture resistance under the CPFT of more than 250 ft-lb/in$^3$ for a 1.0 mil thick piece of material.

Another measure of the puncture resistance of the glove of the invention is the Elmendorf tear test under ASTM D-1922. The Elmendorf tear strength is greater than 400 grams for a 1.0 mil thick piece of material, and preferably is in excess of 600 grams.

In addition, the ultimate tensile strength of the material utilized to produce the glove of the invention is in excess of 6000 psi, and preferably is well in excess of 7000 psi.

Two other material properties which are important to a surgeon are the softness and the fluid resistance of the material utilized to make surgical gloves. A surgeon wishes to retain the ability to sense with his fingertips through his glove a scalpel, suture, and various internal organs in a patient's body. The 2% secant modulus under ASTM D-882 is an indication of the "softness" of a material and of the ability of the material to contour around an object so a surgeon can sense with his fingertip the shape of an object. In the puncture resistant surgical glove of the invention the 2% secant modulus under ASTM D-882 is less than 35,000 psi, and preferably is less than 20,000 psi.

With respect to the moisture transmission rate, such rate is preferably less than 8 gm-mil/100in$^2$-day-atm, and is preferably less than 4 gm-mil/100 in$^2$-day-atm. As is well known, the moisture vapor transmission rate (MVTR) is determined utilizing the Mocon test method on Mocon Permatron W-1 equipment.

Although a wide variety of copolymers and other suitable materials can be utilized in the practice of the invention, copolymers such as ethylene copolymers are presently preferred in the practice of the invention. One type of ethylene copolymer is made by copolymerizing ethylene and selected alphaolefins (commonly butene-1, octene-1, hexene 1, 4-methylpentene-1, or combinations of them) using a transition metal catalyst system. In particular, ATTANE ultra low density ethylene-octene copolymer materials can be utilized in the practice of the invention. Such copolymer materials have densities below 0.915 g/cc, which facilitate the surgeon's retention of his sense of touch when wearing gloves fabricated from such copolymers. The ATTANE copolymer material is produced by Dow Chemical Company of Freeport, Tex. 77541. The ATTANE 4001, 4001.01, 4002, 4003, copolymer materials have an ASTM D-1709 dart impact in excess of 600 grams (1.0 mil thick piece of material), have a CPFT puncture force in excess of 200 ft-lb/in (1.0 mil thick piece of material), have an Elmendorf tear strength under ASTM D-1922 in excess of 700 grams (1.0 mil thick piece of material), have an ultimate tensile strength under ASTM D-882 in excess of 7000 psi, have a 2% secant modulus under ASTM D-882 of less than 15,000 psi, and have a MVTR of less than 2 gm-mil/100 in$^2$-day-atm. Another material which can be utilized in the practice of the invention is ULDPE polymer XU 61512.08, also manufactured by Dow Chemical. XU 61512.08 polymer material has a puncture resistance under ASTM D-1709 in excess of 875 grams (for a 1.0 mil thick piece of material), has an Elmendorf tear strength under ASTM D-1922 (for 1.0 mil thick piece of material) in excess of 275 grams, has a CPFT puncture force in excess of 375 ft-lbs/in$^2$ (1.0 mil thick piece of material), and has an ultimate tensile strength under ASTM D-882 in excess of 7,000 psi.

The polymer material or other material utilized to fabricate the puncture resistant surgical glove of the invention can be cut in strips and woven in the manner illustrated in FIG. 2 or can be used in large sheets or sections to form gloves substantially similar in appearance to conventional latex gloves. Gloves can be formed by cutting out two planar pieces or sheets of polymer material shaped like the hand and by then attaching the two pieces of material by heat sealing the peripheral edges of the two pieces together at all points except at the bottom or "wrist" portions of the material where the hand would be inserted in the glove. If a sheet of polymer material is cut into strips and woven together, it is preferred that a "close" weave be utilized. This means that in FIG. 2 there would be no openings or interstices intermediate strips 25 to 32. Strip 32 would be immediately adjacent and touching strip 31, strip 31 would be immediately adjacent and touching strips 32 and 30, etc. Strip 25 would immediately adjacent and touching strip 26, strip 26 would be immediately adjacent and touching strips 25 and 27, etc. Such a close weave is crucial in making the glove puncture resistance. If there are interstices intermediate strips 25 to 32 in the manner shown in FIG. 2, then a needle can readily penetrate the glove through such an opening.

Puncture resistant portion 19 can be attached to an existing glove by gluing the back side of portion 19 onto a portion of the existing glove, or by forming an opening in a glove. The opening generally corresponds in size to portion 19. Portion 19 can then be secured in the glove by attaching the peripheral edges of portion 19 to the glove.

The tactile sensitivity of the gloved fingers of a surgeon is determined by evaluating the non-displacement tactile sensitivity and the displacement tactile sensitivity. The non-displacement tactile sensitivity is the ability of the surgeon to feel his finger contact an object even though the object does not alter the normal shape of the surgeon's finger. For example, when a individual is not wearing a glove and a hair directly contacts and is pulled over a fingertip, the fingertip tingles or is tickled due to the hair even though the hair does not depress, at least visibly, the skin of the fingertip. When the glove worn by a surgeon is sufficiently thin, the surgeon retains at least a portion of this non-displacement tactile sensitivity. In contrast, the displacement tactile sensitivity is the ability of the fingers of the surgeon's hand to detect when the skin on the surgeon's finger is depressed from its normal uncompressed position. For example, when a surgeon grasps a scalpel or other object the fingertips are compressed and contour around the handle of a scalpel. Even when latex gloves are relatively thick, a surgeon or other person normally retains a portion of this displacement tactile sensitivity. In contrast, the non-displacement tactile sensitivity of a surgeon is normally rapidly attenuated as a glove becomes thicker, when fabric liners or metal liners are utilized, etc. It is a particular advantage of the puncture resistant elastomeric gloves of the invention that at least a portion of the non-displacement tactile sensitivity is retained while the puncture resistance of an elastomeric surgeon's glove is greatly increased.

Another significant advantage of the invention is that it permits the utilization of single elastomeric layer gloves which, without the utilization of liners, significantly improve the puncture resistance of a surgeon's glove over conventional latex surgical gloves which have been utilized by surgeons for many decades.

Having described my invention in such terms as to enable those skilled in the art to understand and practice it, and having identified the presently preferred embodiments thereof, I claim:

1. A surgical glove including a plurality of stalls each for one of the digits of a hand, at least one of said stalls including
   (a) a puncture resistant copolymer material section normally positioned over and contacting at least a portion of the inner surface of one of the digits;
   (b) a thin elastic section attached to said first section and extending continuously around and elastically conforming to the digit and maintaining the first puncture resistant section against said portion of the inner surface of the digit;
   said puncture resistant portion comprising a thin elastic polymer material having
   (c) a puncture resistance under ASTM D-1709 of greater than 500 grams for a 1.0 mil thick piece of said polymer;
   (d) an Elmendorf tear strength under ASTM D-1922 of greater than 400 grams for a 1.0 mil thick piece of said polymer;
   (e) a 2% secant modulus under ASTM D-882 of less than 20,000 psi;
   (f) an ultimate tensile strength under ASTM D-882 in excess of 6,000 psi; and,
   (g) a moisture vapor transmission rate of less than three gram-mil per 100 in$^2$,-day-atmosphere,
   said glove when worn permitting said portion of said inner surface to retain displacement and non-displacement tactile sensitivity.

2. A surgical glove including a plurality of stalls each for one of the digits of a hand, at least one of said stalls including
   (a) an elastic puncture resistant portion normally positioned over and contacting at least a portion of the inner surface of the digit;
   (a) elastic section attached to said first section and extending continuously around an elastically conforming to the digit and maintaining the first puncture resistant section against said portion of the inner surface of the digit; said puncture resistant portion comprising a thin panel having a smooth continuous outer surface, said panel having
   (c) a puncture resistance under ASTM D-1709 of greater than 500 grams for a 1.0 mil thick piece of said portion;
   (d) an Elmendorf tear strength under ASTM D-1922 of greater than 400 grams for a 1.0 mil thick piece of said portion; and,
   (e) an ultimate tensile strength under ASTM D-882 in excess of 6,000 psi,
   said glove when worn permitting said portion of said inner surface to retain tactile sensitivity.

3. An elastomeric surgical glove made from a thin polymer material and including a plurality of stalls each for one of the digits of a hand, said polymer having a puncture resistance under ASTMD-1709 of greater than 500 grams for a 1.0 mil thick piece of said polymer, said glove when worn permitting said digits to retain non-displacement and displacement tactile sensitivity.

4. The surgical glove of claim 3 where said polymer material has
   (a) an Elmendorf tear strength under ASTM D-1922 of greater than 400 grams for a 1.0 mil thick piece of said polymer;
   (b) a 2% secant modulus under ASTM D-882 of less than 20,000 psi;
   (c) an ultimate tensile strength under ASTM D-882 in excess of 6,000 psi; and,
   (d) a moisture vapor transmission rate of less than three gram mil per 100 in$^2$-day-atmosphere.

5. The surgical glove of claim 3 wherein said polymer is a thin sheet of material having a smooth continuous outer surface.

6. The surgical glove of claim 4 wherein said polymer is a thin sheet of material having a smooth continuous outer surface.

7. The surgical glove of claim 2 wherein said elastic puncture resistant portion is a sheet of a composite material.

* * * * *